United States Patent [19]

Caspari et al.

[11] Patent Number: 4,890,615

[45] Date of Patent: Jan. 2, 1990

[54] ARTHROSCOPIC SUTURING INSTRUMENT

[75] Inventors: Richard B. Caspari, Maidens, Va.; Arthur F. Trott, Largo; F. Barry Bays, Seminole, both of Fla.

[73] Assignee: Concept, Inc., Largo, Fla.

[21] Appl. No.: 117,158

[22] Filed: Nov. 5, 1987

[51] Int. Cl.⁴ .................. A61B 17/06; A61B 17/04
[52] U.S. Cl. ................................................ 606/146
[58] Field of Search .................. 128/340, 334 R, 321, 128/346; 227/DIG. 1, 19

[56] References Cited

U.S. PATENT DOCUMENTS

| | | | |
|---|---|---|---|
| 919,138 | 4/1909 | Drake et al. | 128/340 |
| 1,037,864 | 9/1912 | Carlson et al. | 128/340 |
| 1,449,087 | 3/1923 | Bugbee | 128/340 |
| 1,635,066 | 4/1927 | Wells | 128/334 R |
| 1,815,725 | 7/1931 | Pilling et al. | 128/334 R |
| 1,822,330 | 9/1931 | Ainslie | 128/334 R |
| 1,856,721 | 5/1932 | Nagelmann | 128/334 R |
| 2,959,172 | 11/1960 | Held | 128/340 |
| 3,013,559 | 12/1961 | Thomas | 128/340 |
| 3,470,875 | 10/1969 | Johnson | 128/340 |
| 3,840,017 | 10/1974 | Violante | 128/340 |
| 3,842,840 | 10/1974 | Schweizer | 128/340 |
| 3,901,244 | 8/1975 | Schweizer | 128/334 R |
| 3,946,740 | 3/1976 | Bassett | 128/340 |
| 4,064,881 | 12/1977 | Meredith | 128/325 |
| 4,164,225 | 8/1979 | Johnson et al. | 128/340 |
| 4,169,476 | 10/1979 | Hiltebrandt | 128/346 |
| 4,224,947 | 9/1980 | Fukuda | 128/340 |
| 4,312,337 | 1/1982 | Donohue | 128/340 |
| 4,493,323 | 1/1985 | Albright et al. | 128/340 |
| 4,596,249 | 6/1986 | Freda et al. | 128/340 |
| 4,602,635 | 7/1986 | Mulhollan et al. | 128/340 |
| 4,621,640 | 11/1986 | Mulhollan et al. | 128/340 |
| 4,633,869 | 1/1987 | Schmieding | 128/346 |
| 4,643,178 | 2/1987 | Nastari et al. | 128/92 VK |

Primary Examiner—Edward M. Coven
Assistant Examiner—Gary Jackson
Attorney, Agent, or Firm—Epstein, Edell & Retzer

[57] ABSTRACT

A suturing instrument for use in arthroscopic surgery includes a hollow needle for penetrating tissue to be sutured within the body while the tissue is clamped between relatively movable jaws, and a suture feed mechanism for feeding suture material through the hollow needle such that the jaws can be opened and the suturing instrument withdrawn from the body pulling the free end segment of the suture material with the instrument. A knot can be tied in the suture material externally of the body and the knot moved back into the body at a position adjacent the tissue.

22 Claims, 3 Drawing Sheets

ARTHROSCOPIC SUTURING INSTRUMENT

BACKGROUND OF THE INVENTION

1. Field of the Invention

The present invention pertains to suturing instruments and, more particularly, to instruments for arthroscopic suturing of tissue within the body without requiring open surgery.

2. Discussion of the Prior Art

Arthroscopic surgery, which is used herein to encompass surgery on various parts of the body requiring only small incisions or portals for insertion of diagnostic and surgical instruments manipulated externally of the body as well as such surgery performed on joints, is preferable over open surgery to avoid the trauma associated with large incisions as well as the hospitalization and prolonged recovery periods required with open surgery and is used whenever possible to achieve the same results as open surgery without the disadvantages thereof. Arthroscopic techniques include internal viewing for diagnosis and identification of problems as well as surgical operations such as meniscus removal or repair, shaving of irregular, roughened patella and other surfaces and articular surface smoothing. While many surgical operations that previously required open surgery can now be performed by arthroscopic surgery, there remain operations that still require open surgery due to the need for direct suturing, such as major ligament repair and cartilage repair.

U.S. Pat. Nos. 4,493,323 to Albright et al, and Nos. 4,602,635 and 4,621,640 to Mulhollan et al are representative of prior art instruments for internal suturing without requiring open surgery; however, such instruments have the disadvantages of requiring multiple instrument manipulation and movement of needles carrying sutures entirely through tissue to be sutured. The instrument of the Albright et al patent includes a pair of needles forced outwardly through the end of a tube by a plunger to penetrate and extend through the tissue to be sutured and through the skin to permit the needles to be grasped by the surgeon and pulled to position a suture thread loop attached to the needles. The instrument of the Mulhollan et al patent 4,621,640 includes a curved needle carried by a pivotal head movable to cause the needle to be set in the tissue to be sutured, the needle then being released and the instrument withdrawn to allow insertion of another instrument to pull the needle through. The Mulhollan et al patent 4,602,635 relates to an instrument for tying knots in sutures in a manipulation area external of the body after the sutures are sewn through the tissue and then pushing the knots into place adjacent the tissue.

U.S. Pat. No. 919,138 to Drake et al, No. 3,840,017 to Violante, No. 4,224,947 to Fukuda, and No. 4,643,178 to Nastari et al are representative of prior art suturing instruments wherein sutures are passed through hollow needles after the needles penetrate through tissue to be sutured, such suturing instruments having the disadvantage of requiring grasping of the suture material and, thus, being useful only in open surgery and not in arthroscopic surgery.

U.S. Pat. Nos. 1,815,725 to Pilling et al, No. 3,470,875 to Johnson, No. 3,842,840 to Schweizer, No. 3,946,740 to Bassett and No. 4,164,225 to Johnson et al are representative of prior art suturing instruments having pivoted, scissor-like arms with a needle forced through the end of an arm, through tissue to be sutured and into the end of the other arm where the suture is grasped or clampled, such suturing instruments having the disadvantage of being of a structural design to prevent their use in arthroscopic surgery.

U.S. Pat. No. 4,312,337 to Donohue discloses an instrument for drilling and wiring bones having scissor-like arms carrying cannula sections through which a wire is passed, the wire being cut and tied after the cannula sections are withdrawn. The scissor-like structure permits this instrument to be used only in open surgery and not in arthroscopic surgery.

Another scissor-like instrument for suturing is disclosed in U.S. Pat. No. 4,596,249 to Freda et al, the instrument having a hook passing through tissue to engage a suture and pull it back through the tissue, the instrument not being useful in arthroscopic surgery due to its scissor-like structure.

SUMMARY OF THE INVENTION

Accordingly, it is a primary object of the present invention to overcome the disadvantages of the prior art by providing a suturing instrument for use in arthroscopic surgery.

Another object of the present invention is to permit suturing during surgery with an instrument that can be introduced through an arthroscopic tube or cannula to set a suture in tissue and withdrawn to permit tying of a knot and tightening of the knot adjacent the tissue.

A further object of the present invention is to construct an instrument of setting sutures during arthroscopic surgery that can be manipulated by a surgeon in a manner similar to a conventional grasper or forceps.

The present invention has another object in that suture material can be fed through a hollow needle after the needle has been forced through tissue to be sutured allowing the suture material to be pulled from the body, a knot tied therein and the knot moved back into the body adjacent the tissue.

Some of the advantages of the present invention over the prior art are that suturing can be accomplished without requiring open surgery, the suturing instrument is simple in structure facilitating its use in surgery, and the suturing instrument permits accurate placement of sutures by the jaws clamping tissue to be sutured while the hollow needle penetrates the tissue.

The present invention is generally characterized in a suturing instrument for use in arthroscopic surgery including a stationary member having an elongate tube with a proximal end and a distal end and a stationary handle member extending from the proximal end of the tube and adapted to be gripped by a surgeon, a movable handle member mounted on the stationary member and adapted to be gripped by a surgeon to be movable toward and away from the stationary handle member, a jaw tip disposed at the distal end of the tube for clamping and penetrating tissue to be sutured including a first jaw having a hollow needle extending substantially transversely therefrom, a second jaw having an opening therein, and means mounting the first and second jaws to permit relative movement of the jaws toward and away from each other to define closed and open positions, respectively, the needle extending into the opening in the second jaw when the jaw tip is in the closed position, a connector connecting the movable handle member with the jaw tip to cause relative movement of the first and second jaws as the movable handle member is moved toward and away from the stationary handle member, and a suture material feeding unit for feeding suture material along the tube to the needle and, with the jaw tip in the closed position, through the needle and the opening in the second jaw whereby suture material can be passed through tissue to be sutured when the jaw tip is in the closed position and, thereafter, when the jaw tip is in the open position, the suture material can be drawn away from the tissue to be sutured.

Other objects and advantages of the present invention will become apparent from the following description of the preferred embodiment taken in conjunction with the accompanying drawings.

DESCRIPTION OF THE PREFERRED EMBODIMENT

Figures 1, 2, 3, 4, 5, 6:
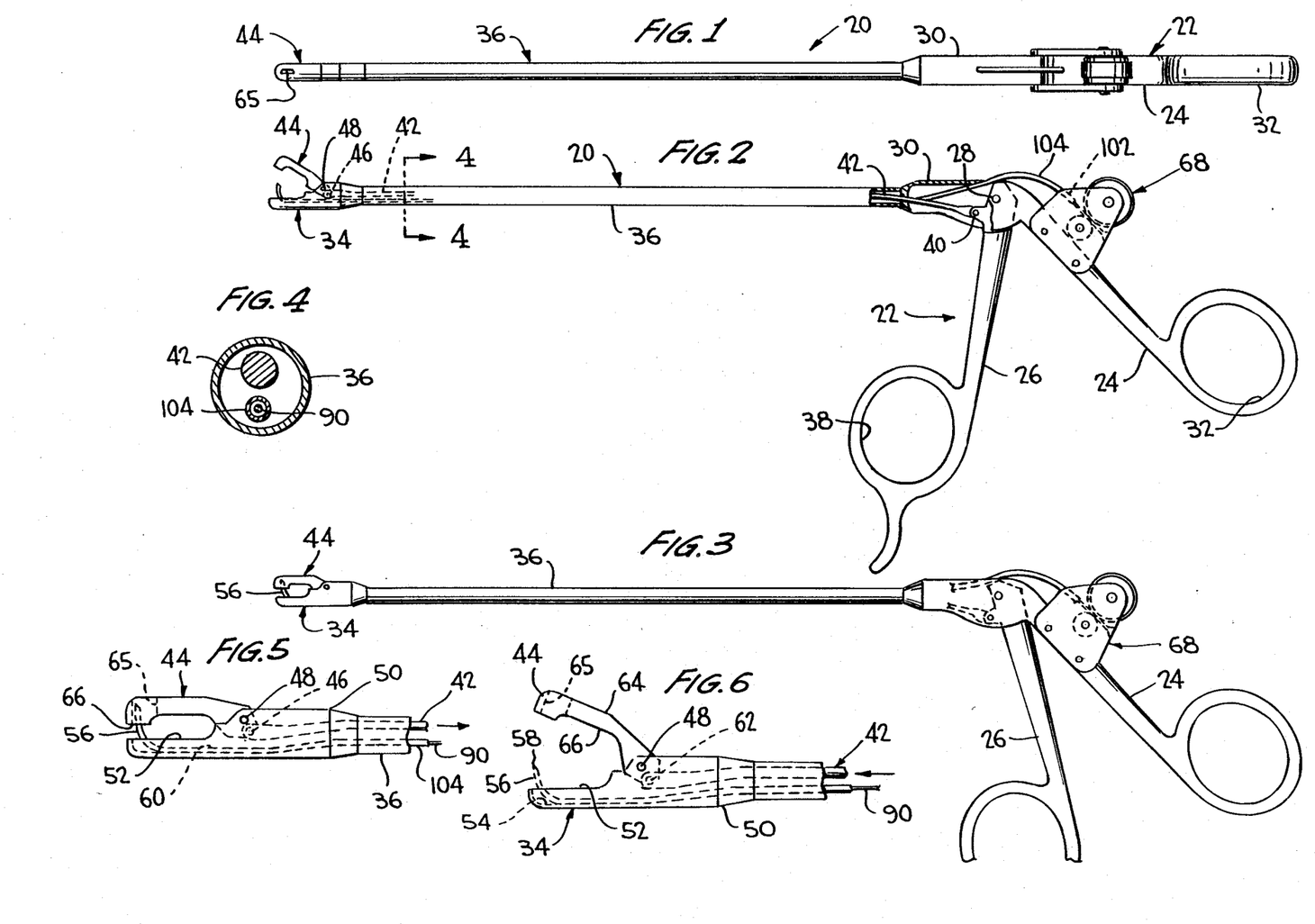
FIG. 1 is a top view of a suturing instrument according to the present invention.
FIGS. 2 and 3 are side elevations of the suturing instrument of the present invention with the jaws in open and closed positions, respectively.
FIG. 4 is a sectional view taken along line 4—4 of FIG. 2.
FIGS. 5 and 6 are broken side views of the jaws of the suturing instrument of the present invention in closed and open positions, respectively.

A suturing instrument 20 according to the present invention is illustrated in FIGS. 1, 2 and 3 and includes a handle 22 formed of a stationary handle member 24 and a movable handle member 26 pivotally mounted to stationary handle member 24 on a pivot pin 28 secured in a hub 30. The stationary handle member 24 has a thumb ring 32 at one end and forms part of a stationary member including hub 30, a distal stationary jaw 34 and an elongate tube or barrel 36. The movable handle member 26 has a finger ring 38 at one end and extends through an opening in the bottom of the hub to be mounted on pivot pin 28. A flange 40 extends distally from movable handle member 26 and is pivotally attached to a connector rod 42 extending within tube 36 to the distal end thereof where the rod is connected to a pivotal jaw 44 via a pin 46, the jaw 44 being pivotally mounted on a pin 48 secured to the stationary jaw 34 to pivot toward and away from the stationary jaw. The stationary and movable handle members and the elongate tube terminating at a distal end in a jaw tip are structurally similar to conventional grasper and forceps-type microsurgical instruments commonly used for arthroscopic surgery.

In accordance with the present invention, the stationary jaw 34 includes a hollow tip 50, as best shown in FIGS. 5 and 6, secured to the distal end of tube 36, the tip being cut away to define a peripheral wall 52 for engaging tissue to be sutured and a recess 54 in which is secured a hollow, tubular needle 56 having a bevelled cutting tip 58 to penetrate tissue to be sutured. The needle 56 is smoothly curved such that the portion terminating at tip 58 extends substantially transversely from a portion 60 secured in recess 54 and, thus, extends substantially transversely from the plane of the ends of the peripheral wall 52 of the stationary jaw. Pivotal jaw 44 is pivotally mounted to tip 50 on pin 48 and has an inner end 62 attached to rod 42 via pin 46 and an outer end 64 with an aperture 65 therethrough aligned with needle 56 such that needle tip 58 will extend into the aperture when the jaws are closed as shown in FIG. 5. The pivotal jaw 44 has an inner surface 66 facing the surface of peripheral wall 52 of the stationary jaw such that tissue to be sutured can be clamped between surfaces 52 and 66 when the jaws are closed.

Figures 7, 8:
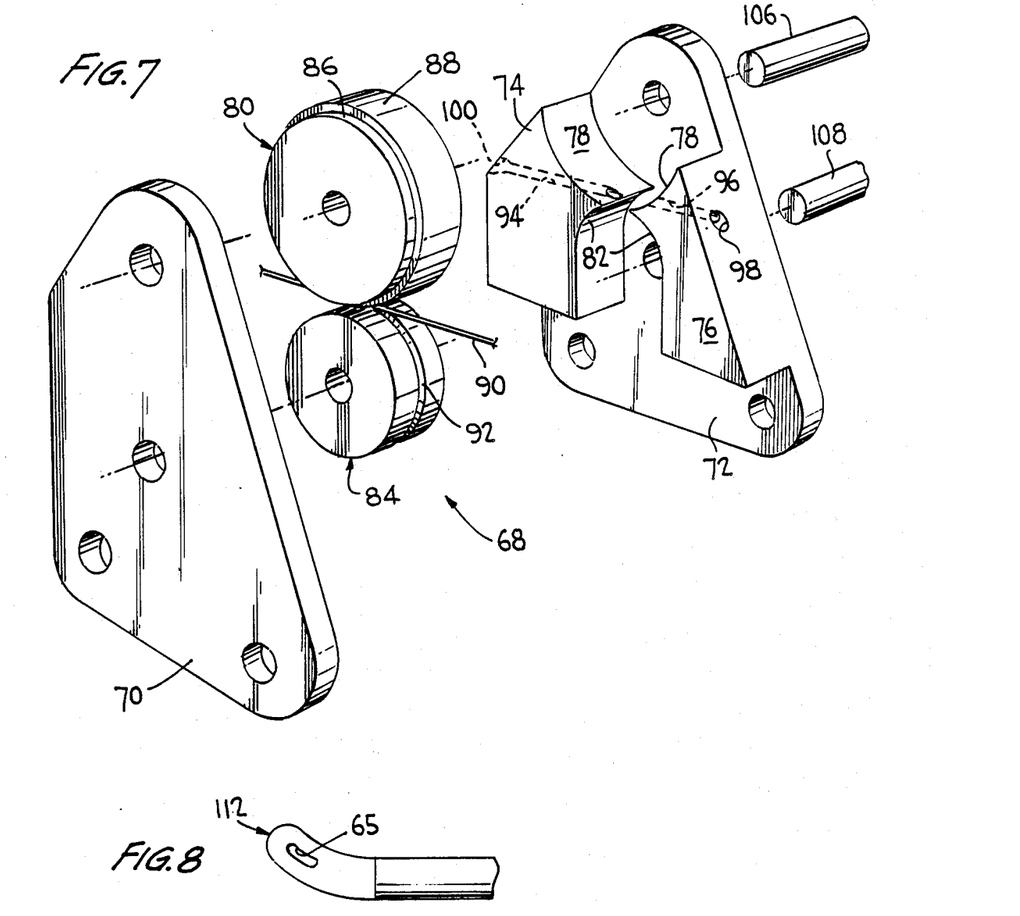
FIG. 7 is an exploded view of the suture feed mechanism of the suturing instrument of the present invention.
FIGS. 8, 9 and 10 are top views of right-hand, straight and left-hand jaw tips for the suturing instrument of the present invention.

A suture feed mechanism 68 is mounted on stationary handle member 24 and includes, as best shown in FIG. 7, mounting plates 70 and 72 having a pair of spaced lower holes to receive screws to secure the plates to opposite sides of the stationary member. Mounting plate 72 has bosses 74 and 76 thereon to define curved upper surfaces 78 forming a recess for receiving a drive roller 80 and curved lower surfaces 82 forming a recess for receiving an idler roller 84. Roller 80 has opposite side flanges 66 forming an central channel receiving a peripheral ring 88 of high friction, autoclavable material, such as silicone rubber, for engaging a suture material 90 that passes between rollers 80 and 84 riding in a peripheral, V-shaped groove 92 in roller 84. Aligned bores 94 and 96 extend through bosses 74 and 76, respectively, to guide suture material 90 therethrough with bore 96 having a countersunk outlet 100 to receive the proximal end 102 of a length of tubing 104 that runs through an opening in the top of hub 30 and through tube 36 below rod 42, as shown in FIGS. 2 and 4, to terminate at needle 56. Needle 56 and tubing 104 can be formed of single length of stainless steel tubing or can be two pieces joined at the distal end of the suturing instrument 20. Rollers 80 and 84 are rotatably mounted on pins 106 and 108, respectively, secured in holes in plates 70 and 72.

With the exception of ring 88, all components of the suturing instrument 20 are preferably constructed of stainless steel; and, with the ring made of silicone rubber, the entire instrument is autoclavable.

Figure 9:
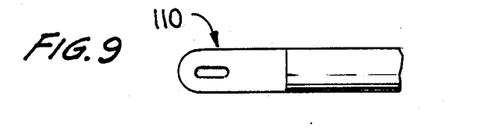
Figure 10:
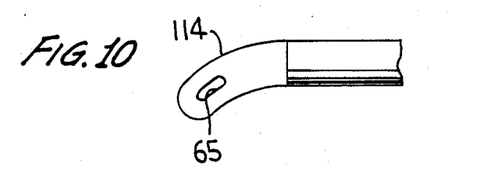
Figure 11:
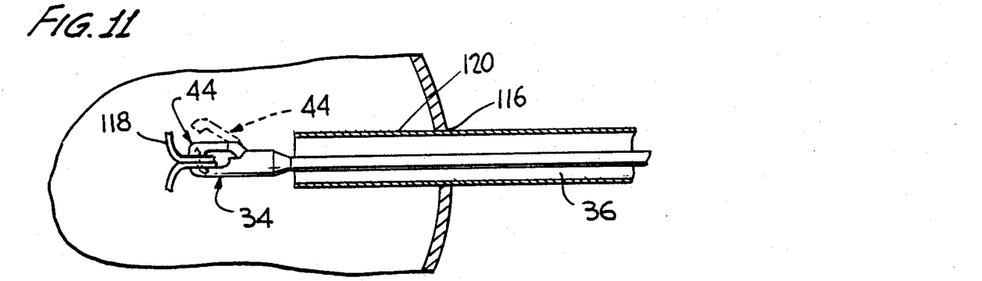
FIGS. 11, 12, 13, 14 15 and 16 illustrate the method of use of the suturing instrument of the present invention.

The jaws of the suturing instrument can extend from the distal end of the tube 36 in alignment with the longitudinal axis thereof, as described above and shown at 110 in FIG. 9, or can be bent to the right or left, as shown in FIGS. 8 and 10, at 112 and 114, respectively to extend at an angle to the longitudinal axis of tube 36. The pivot pins 46 and 48 are positioned at the same place in the straight, right hand and left hand configurations with the stationary and pivotal jaws bent beyond pivot pin 48. Aperture 65 in the pivotal jaws are oblong to facilitate accommodation of the needle 56 when the jaws are closed clamping tissue to be sutured therebetween. While an aperture is preferred to increase structure integrity of the pivotal jaw, an opening of any shape, such as a slot, can be used.

Use and operation of the suturing instrument will be described with reference to FIGS. 11–16. The suturing instrument 20 is inserted into the body through an incision or portal 116 in the skin and moved to the tissue to be sutured 118. In most cases, the suturing instrument will be inserted through a tube or cannula 120, and positioning of the suturing instrument is accomplished using conventional arthroscopic instruments which permit television viewing of the surgical site for inspection, diagnosis and surgery. The jaws are opened by pivoting movable handle member 26 away from stationary handle member 24 using the finger and thumb, respectively, to cause pivotal jaw 44 to pivot away from stationary jaw 34 due to movement of rod 42, as shown in FIGS. 2 and 6 and in dashed lines in FIG. 11. When the jaws are properly positioned on opposite sides of tissue 118 to be sutured, the movable handle member 26 is moved toward the stationary handle member 24 by squeezing the finger and thumb together causing the tissue engaging surfaces 52 and 66 of the jaws to clamp the tissue while needle 56 is forced through the tissue and into opening 65 in pivotal jaw 44. Accordingly, the suture instrument operates as a punch as needle 56 penetrates through the tissue.

Figure 12:
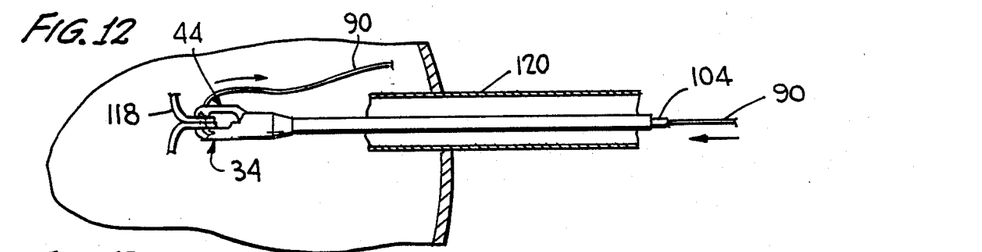
Figure 13:
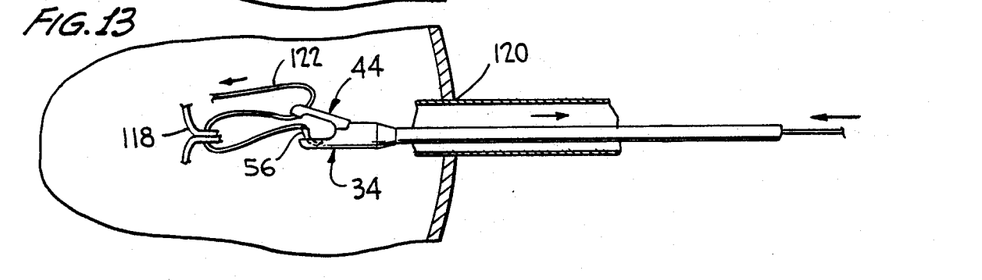

After the jaws are operated to punch needle 56 through the tissue 118, suture material 90 is forced through the needle to exit from the open tip of the needle and pass through the opening 65 in pivotal jaw 44, as shown in FIG. 12. To accomplish this, the suture material is fed through inlet 98 of the suture feed mechanism, and the drive roller 80 is rotated clockwise, looking at FIG. 3, with a finger or thumb. The ring 88 engages the suture material which rides in the groove 92 in idler roller 84, and the rollers cooperate to grip and move the suture material. In this manner, the suture material is fed through outlet 100 of the suture feed mechanism and through tubing 104 and needle 56. In practice, the suture material will be fed through the needle and backed off to be adjacent to the needle tip but within the needle prior to insertion of the suturing instrument into the portal 116 such that minimal rotation of drive roller 80 is required to cause a length of the suture material to extend out of needle 56, as shown in FIG. 12.

Figure 14:
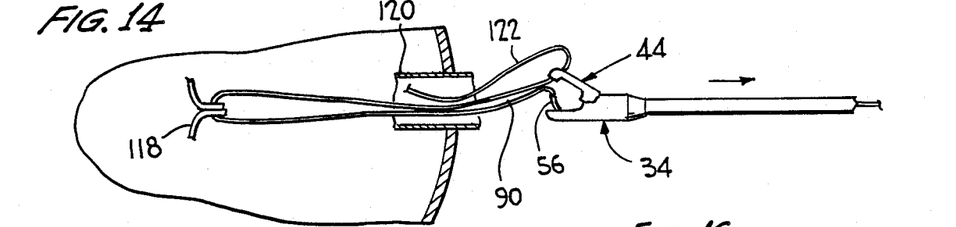

Once a sufficient length of the suture material is fed through as shown in FIG. 12, the jaws are opened to withdraw the needle back through the tissue; and, the suturing instrument 20 is moved away from the tissue 118 causing a free end segment 122 of the suture material to be folded back on itself, the edge of the aperture 65 in the pivotal jaw 44 catching the suture material to pull the free end segment of the suture material out while the suture material is also fed toward the jaws by driver roller 80 such that the suturing instrument can be withdrawn from the body leaving the suture in place through the tissue as shown in FIG. 14.

Figure 15:
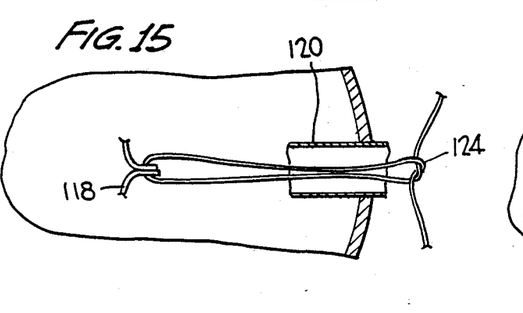
Figure 16:
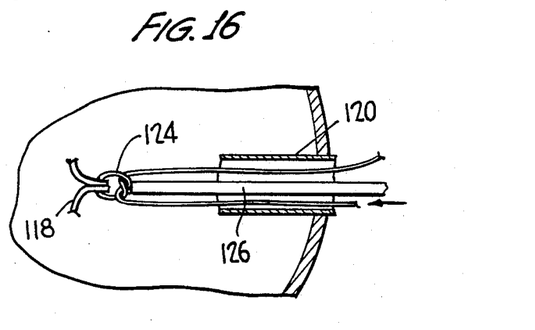

With the ends of the suture outside the body, a knot 124 can be tied by the surgeon in any conventional fashion, as shown in FIG. 15; and, the knot can be pushed through the cannula 120 using a throw stick 126 to a position adjacent the tissue 118, as shown in FIG. 16. The knot can now be tightened by pulling on either or both ends of the suture material. Several knots may be tied, and the suture material is then cut with the use of a microsurgical scissors allowing the cut ends of the suture material to be withdrawn through the tube 120.

As will be appreciated from the above, the suturing instrument of the present inventin operates as a punch to allow feeding of suture material through tissue to be sutured within the body, knotting the suture material externally of the body and placing and tightening the knot adjacent the tissue without requiring open surgery thereby permitting repair of ligaments and meniscus, among other tissues, arthroscopically.

Inasmuch as the present invention is subject to many variations, modifications and changes in detail, it is intended that all subject matter discussed above or shown in the accompanying drawings be interpreted as illustrative only and not to be taken in a limiting sense.

What is claimed is:

1. A suturing instrument for use in surgery comprising
   a member including an elongate tube having a proximal end and a distal end and a handle member extending from said proximal end of said tube and adapted to be gripped by a surgeon;
   a hollow needle extending from said distal end of said member for penetrating tissue to be sutured; and
   suture material feeding means for feeding suture material along said tube and through said needle whereby suture material can be passed through tissue to be sutured, said suture material feeding means including a roller feed mechanism mounted on said member having inlet means for receiving suture material, outlet means for supplying suture material to said tube and roller means rotatable for drive suture material from said inlet means through said outlet means and said tube to said hollow needle for passage therethrough.

2. A suturing instrument as recited in claim 1 and further comprising tubing means disposed within said elongate tube and connected with said outlet means and said hollow needle for passage therethrough of suture material.

3. A suturing instrument as recited in claim 1 wherein said roller means includes a drive roller having a peripheral surface and an idler roller having a peripheral surface adjacent said peripheral surface of said drive roller, suture material passing between said drive and idler rollers to be engaged and driven by said peripheral surface of said driver roller.

4. A suturing instrument as recited in claim 3 wherein said drive roller has a ring of silicone rubber around said peripheral surface to engage suture material.

5. A suturing instrument as recited in claim 4 wherein said idler roller has a groove in said peripheral surface to receive suture material.

6. A suturing instrument for use in arthroscopic surgery comprising
   a stationary member including an elongate tube having a proximal end and a distal end and a stationary handle member extending from said proximal end of said tube and adapted to be gripped by a surgeon;
   a movable handle member mounted on said stationary member and adapted to be gripped by a surgeon to be movable toward and away from said stationary handle member;
   jaw means disposed at said distal end of said tube for clamping and penetrating tissue to be sutured including a first jaw having a hollow needle extending therefrom, a second jaw having an opening therein, and means mounting said first and second jaws to permit relative movement of said jaws toward and away from each other to define closed and open positions, respectively, said needle extending into said opening in said second jaw when said jaw means is in said closed position;
   connector means connecting said movable handle member with said jaw means to cause relative movement of said first and second jaws as said movable handle member is moved toward and away from said stationary handle member; and
   suture material feeding means for feeding suture material along said tube to said needle and, with said jaw means in said closed position, through said needle and said opening in said second jaw whereby suture material can be passed through tissue to be sutured when said jaw means is in said closed position and, thereafter, when said jaw means is in said open position, the suture material can be drawn away from the tissue to be sutured.

7. A suturing instrument as recited in claim 6 wherein said first jaw extends from said distal end of said tube and has a tissue engaging surface, said second jaw has a tissue engaging surface facing said tissue engaging surface of said first jaw, and said mounting means includes means for mounting said second jaw for pivotal movement relative to said first jaw.

8. A suturing instrument as recited in claim 7 wherein said opening in said second jaw is an aperture having an edge for engaging suture material passing therethrough when said suturing instrument is moved away from the tissue to be sutured.

9. A suturing instrument as recited in claim 6 wherein said stationary member includes a hub disposed between said proximal end of said tube and said stationary handle member, said movable handle member is pivotally mounted on said stationary member at said hub, and, said movable and stationary handle members extend from said hub at angles to the longitudinal axis of said tube.

10. A suturing instrument as recited in claim 9 wherein said suture material feeding means includes a feed mechanism disposed on said stationary member and tubing means connected with feed mechanisms and said hollow needle for supplying suture material fed by said feed mechanism to and through said hollow needle.

11. A suturing instrument as recited in claim 10 wherein said hub has an opening therein and said tubing means extends through said hub opening and through said elongate tube.

12. A suturing instrument as recited in claim 11 wherein said hollow needle and said tubing means are made of a single length of metal tubing curved at said first jaw to terminate at a beleved end defining a tip for said hollow needle.

13. A suturing instrument as recited in claim 12 wherein said feed mechanism is mounted on said stationary handle member and includes a drive roller and an idler roller for feeding suture material through said length of tubing.

14. A suturing instrument for use in arthroscopic surgery comprising
a stationary member including an elongate tube having a proximal end and a distal end and a stationary handle member extending from said proximal end of said tube and adapted to be gripped by a surgeon;
a movable handle member mounted on said stationary member and adapted to be gripped by a surgeon to be movable toward and away from said stationary handle member;
jaw means disposed at said distal end of said tube for clamping and penetrating tissue to be sutured including a first jaw having a hollow needle extending substantially transversely therefrom, a second jaw having an opening therein, and means mounting said first and second jaws to permit relative movement of said jaws toward and away from each other to define closed and open positions, respectively, said needle extending into said opening in said second jaw when said jaw means is in said closed position;
connector means connecting said movable handle member with said jaw means to cause relative movement of said first and second jaws as said movable handle member is moved toward and away from said stationary handle member; and
suture material feeding means for feeding suture material along said tube to said needle and, with said jaw means in said closed position, through said needle and said opening in said second jaw whereby suture material can be passed through tissue to be sutured when said jaw means is in said closed position and, thereafter, when said jaw means is in said open position, the suture material can be drawn away from the tissue to be sutured, said suture material feeding means including a roller feed mechanism mounted on said stationary member having an inlet for receiving suture material, an outlet for exit of suture material and roller means rotatable to feed suture material from said inlet to said outlet, and tubing means connected with said outlet of said roller feed mechanism and said hollow needle for passage therethrough of suture material.

15. A suturing instrument as recited in claim 14 wherein said tubing means is disposed within said elongate tube.

16. A suturing instrument as recited in claim 15 wherein said first jaw extends from said distal end of said tube and has a tissue engaging surface, said second jaw has a tissue engaging surface facing said tissue engaging surface of said first jaw, and said mounting means includes means for mounting said second jaw for pivotal movement relative to said first jaw.

17. A suturing instrument as recited in claim 1 wherein said first and second jaws extend from said distal end of said tube in alignment with the longitudinal axis of said tube.

18. A suturing instrument as recited in claim 16 wherein said first and second jaws extend from said distal end of said tube at an angle to the longitudinal axis of said tube.

19. A suturing instrument as recited in claim 16 wherein said opening in said second jaw is an aperture having an edge for engaging suture material passing therethrough when said suturing instrument is moved away from the tissue to be sutured.

20. A suturing instrument as recited in claim 19 wherein said roller means includes a drive roller having a peripheral surface and an idler roller having a peripheral surface adjacent said peripheral surface of said drive roller, suture material passing between said drive and idler rollers to be engaged and driven by said peripheral surface of said driver roller.

21. A suturing instrument as recited in claim 20 wherein said drive roller has a ring of silicone rubber around said peripheral surface to engage suture material.

22. A suturing instrument as recited in claim 21 wherein said idler roller has a groove in said peripheral surface to receive suture material.

* * * * *

UNITED STATES PATENT AND TRADEMARK OFFICE
CERTIFICATE OF CORRECTION

PATENT NO. : 4,890,615

DATED : January 2, 1990

INVENTOR(S) : Richard B. Caspari, Arthur F. Trott and F. Barry Bays

It is certified that error appears in the above-identified patent and that said Letters Patent is hereby corrected as shown below:

Column 2, line 2, "clampled" should read --clamped--;
         line 29, "of" should read --for--.

Column 4, line 21, "66" should read --86--;
         line 55, "ture" should read --tural--.

Column 5, line 56 "inventin" should read --invention--.

Column 6, line 16, "for" should read --to.

Signed and Sealed this

Ninth Day of April, 1991

*Attest:*

HARRY F. MANBECK, JR.

*Attesting Officer*      *Commissioner of Patents and Trademarks*

REEXAMINATION CERTIFICATE (2134th)
United States Patent [19]
Caspari et al.

[11] B1 4,890,615
[45] Certificate Issued Nov. 16, 1993

[54] ARTHROSCOPIC SUTURING INSTRUMENT

[75] Inventors: Richard B. Caspari, Maidens, Va.; Arthur F. Trott, Largo; F. Barry Bays, Seminole, both of Fla.

[73] Assignee: Linvatec Corporation

Reexamination Request:
No. 90/002,702, Apr. 20, 1992

Reexamination Certificate for:
Patent No.: 4,890,615
Issued: Jan. 2, 1990
Appl. No.: 117,158
Filed: Nov. 5, 1987

[51] Int. Cl.$^5$ .................................................. A61B 17/00
[52] U.S. Cl. ..................................... 606/146; 606/139
[58] Field of Search ............... 606/146, 147, 144, 145

[56] References Cited

U.S. PATENT DOCUMENTS 373,372   11/1987   King .
786,000    8/1903   Botkin .
854,147    4/1906   Cavillon et al. .
1,066,317  7/1913   Pirnat .
2,396,180  3/1946   Karle .
2,414,746  1/1947   Karle .
2,611,366  9/1952   Mull .
2,808,055 10/1957   Thayer .............................. 128/340

FOREIGN PATENT DOCUMENTS 630693   12/1949   United Kingdom .

*Primary Examiner*—Stephen C. Pellegrino

[57] ABSTRACT

A suturing instrument for use in arthroscopic surgery includes a hollow needle for penetrating tissue to be sutured within the body while the tissue is clamped between relatively movable jaws, and a suture feed mechanism for feeding suture material through the hollow needle such that the jaws can be opened and the suturing instrument withdrawn from the body pulling the free end segment of the suture material with the instrument. A knot can be tied in the suture material externally of the body and the knot moved back into the body at a position adjacent the tissue.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 6-16 and 18-22 is confirmed.

Claims 1 and 2 are determined to be patentable as amended.

Claim 3-5 and 17, dependent on an amended claim, are determined to be patentable.

New claims 23-31 are added and determined to be patentable.

1. A suturing instrument for use in surgery comprising:
   a member including an elongate tube having a proximal end and a distal end and a handle member extending from said proximal end of said tube and adapted to be gripped by a surgeon;
   a hollow needle extending from said distal end of said member for penetrating tissue to be sutured; and
   suture material feeding means for feeding suture material along said tube and through said needle whereby suture material can be passed through tissue to be sutured, said suture material feeding means including a roller feed mechanism mounted on said member having *an* inlet *bore* means for receiving suture material, *an* outlet *bore* means for supplying suture material to said tube and roller means rotatable for [drive] *driving* suture material from said inlet *bore* means through said outlet *bore* means and said tube to said hollow needle for passage therethrough.

2. A suturing instrument as recited in claim 1 and further comprising tubing means disposed within said elongate tube and connected with said outlet *bore* means and said hollow needle for passage therethrough of suture material.

*23. A suturing instrument for use in surgery comprising:*
   *a member including an elongate tube having a proximal end and a distal end and a handle member extending from said proximal end of said tube and adapted to be gripped by a surgeon;*
   *a hollow needle extending from said distal end of said member for penetrating tissue to be sutured; and*
   *suture material feeding means for feeding suture material along said tube and through said needle whereby suture material can be passed through tissue to be sutured, said suture material feeding means including a roller feed mechanism mounted on said handle member having an inlet bore means for receiving suture material, an outlet bore means for supplying suture material to said tube and roller means rotatable to drive material from said inlet bore means through said outlet bore means and said tube to said hollow needle for passage therethrough, said inlet bore means, said roller means, and said outlet bore means combining to automatically align and guide suture material through said suture material feeding means.*

*24. A spoolless suturing instrument for use in surgery comprising:*
   *a member including an elongate tube having a proximal end and a distal end and a handle member extending from said proximal end of said tube and adapted to be gripped by a surgeon;*
   *a hollow needle extending from said distal end of said member for penetrating tissue to be sutured; and*
   *suture material feeding means for feeding suture material along said tube and through said needle whereby suture material can be passed through tissue to be sutured, said suture material feeding means including a roller feed mechanism mounted on said handle member having an inlet guide means for receiving suture material from said surgeon, an outlet guide means for supplying suture material to said tube and roller means rotatable to drive suture material from said inlet guide means through said outlet guide means and said tube to said hollow needle for passage therethrough, said inlet guide means, said roller means, and said outlet guide means combining to automatically align and guide suture material through said suture material feeding means.*

*25. A suturing instrument for use in surgery comprising:*
   *a member including an elongate tube having a proximal end and a distal end and a handle member extending from said proximal end of said tube and adapted to be gripped by a surgeon;*
   *a hollow needle extending from said distal end of said member for penetrating tissue to be sutured;*
   *suture material feeding means for feeding suture material along said tube and through said needle whereby suture material can be passed through tissue to be sutured, said suture material feeding means including a roller feed mechanism mounted on said handle member and a plurality of aligned bore means adapted to mechanically align and guide said suture material into said roller feed mechanism and thereafter, into said tube.*

*26. A suturing instrument as recited in claim 1, 23, 24, 25 or 31 for use in arthroscopic surgery.*

*27. A suturing instrument as recited in claim 1, 23, 24, 25 or 31 for use in endoscopic surgery.*

*28. A suturing instrument as recited in claim 23, 24, 25 or 31 wherein said roller feed mechanism includes a drive roller having a peripheral surface and an idler roller having a peripheral surface adjacent said peripheral surface of said drive roller, suture material passing between said drive and idler rollers to be engaged and driven by said peripheral surface of said drive roller.*

*29. A suturing instrument as recited in claim 28 wherein said drive roller has a ring of elastomeric material around said peripheral surface to engage suture material.*

*30. A suturing instrument as recited in claim 29 wherein said idler roller has a groove in said peripheral surface to receive suture material.*

*31. A suturing instrument for use in surgery comprising:*
   *a member including an elongate tubing having a proximal end and a distal end and a handle member extending from said proximal end of said tube;* a hollow needle extending from said distal end of said member for penetrating tissue to be suture;

suture material feeding means for feeding suture material along said tube and through said needle whereby suture material can be passed through tissue to be sutured, said suture material feeding means including a roller feed mechanism mounted on said handle member and an alignment means adapted to automatically align and guide said suture material into said roller feed mechanism and thereafter, into said tube, wherein said alignment means comprises an inlet bore means and an outlet bore means.

* * * * *